(12) United States Patent
Figovsky et al.

(10) Patent No.: US 6,407,198 B1
(45) Date of Patent: Jun. 18, 2002

(54) CYCLOCARBONATE GROUPS CONTAINING HYDROXYAMINE OLIGOMERS FROM EPOXYCYLCLOCARBONATES

(75) Inventors: Oleg Figovsky; Leonid Shapovalov; Nelly Blank, all of Haifa; Florida Buslov, Kiryat Ata, all of (IL)

(73) Assignees: Chemonol Ltd.; Polymate Ltd., both of (IL)

( * ) Notice: Subject to any disclaimer, the term of this patent is extended or adjusted under 35 U.S.C. 154(b) by 0 days.

(21) Appl. No.: 09/622,960

(22) PCT Filed: Nov. 24, 1999

(86) PCT No.: PCT/IB99/01885

§ 371 (c)(1),
(2), (4) Date: Aug. 24, 2000

(87) PCT Pub. No.: WO00/42033

PCT Pub. Date: Jul. 20, 2000

(30) Foreign Application Priority Data

Jan. 14, 1999 (EP) .............................................. 99100586

(51) Int. Cl.[7] .............................................. C08G 64/00
(52) U.S. Cl. ...................................... 528/196; 528/198
(58) Field of Search ................................ 528/196, 198

(56) References Cited

U.S. PATENT DOCUMENTS 4,585,566 A    4/1986  Wollenberg
5,175,231 A   12/1992  Rapport et al.
5,340,889 A    8/1994  Crawford et al.

FOREIGN PATENT DOCUMENTS

DE    3624314    1/1988
EP    0303158    2/1989
EP    0535794    7/1993
WO    9858004   12/1998

OTHER PUBLICATIONS

"Chemical Toughening of Epoxies. I. Structural Modification of Epoxy Resins by Reaction with Hydroxy–Terminated Poly(Butadiene–co–Acrylonitrile)"—J. Appl. Polym. Science, vol. 39, No. 7, 1990, pp. 1459–1466, S. Sankaran, M. Chanda.

Database WPI Week 9627 Derwent Publications Ltdl, London, GB; XP002133490—abstract—Nov. 20, 1995.

Database WPI Week 9637 Derwent Publications Ltd., London, GB; XP002133491—abstract—Dec. 20, 1995.

Database WPI Week 8251 Derwent Publications Ltd., London, GB; XP002133492—abstract—Feb. 28, 1982.

*Primary Examiner*—Terressa M. Boykin
(74) *Attorney, Agent, or Firm*—Bierman, Muserlian and Lucas

(57) ABSTRACT

Chemically resistant materials with high mechanical properties are provided by using polycyclocarbonates of special structure. The polycyclocarbonates are prepared by the reaction of oligocyclocarbonates containing ended epoxy groups with primary aromatic diamine.

8 Claims, No Drawings

CYCLOCARBONATE GROUPS CONTAINING HYDROXYAMINE OLIGOMERS FROM EPOXYCYLCLOCARBONATES

TECHNICAL FIELD

The present invention is related to cyclocarbonate oligomers and polymer compounds based on them and, more specifically, to coatings, adhesives, composite materials, sealants, and synthetic leather and to methods of producing such materials.

BACKGROUND OF THE INVENTION

Nonisocyanate polyurethane oligomers and polymers are the product of the reaction of cyclocarbonate oligomers and primary amine oligomers. Typically the cyclocarbonate oligomer react with the primary aliphatic amine oligomer. By this reaction a cross-linked network polymer structure results in which an intermolecular hydrogen bond is formed through the hydroxyl group at the β-carbon atom of the polyurethane chain.

The blockage of carbonyl oxygen considerably lowers the susceptibility of the whole urethane group to hydrolysis. Moreover, materials containing intermolecular hydrogen bonds display chemical resistance 1.5–2 times greater in comparison with materials of similar structure without such bonds.

There is known method of production of linear nonisocyanate polyurethane based on reaction between oligomeric bifunctional cyclocarbonates and primary aliphatic amines (U.S. Pat. No. 5,340,889, published 23.08.94)

There is known method of preparing of nonisociante compounds by mixing polyfunctional cyclocarbonate and primary amine oligomer (O. Figovsky, L. Shapovalov, N. Blank. Monolithic Chemical Resistant Floor Covering Based on Non-Isocyanate Polyurethanes./Corrosion and its control./Proceedings of CORCON-97, Mumbai, India. 1997. v.2 p.757–763.

But it is impossible to prepare nonisocyanate polyurethane materials using aromatic amines and cyclocarbonates because of forming $CO_2$ and low molecular weight of compounds. One of the possible processes for making cyclocarbonates is a reaction between carbon dioxide and an epoxy compound in the presence of a catalyst.

SUMMARY OF THE INVENTION

It is an object of the invention to provide for a new polyfunctional polycarbonate oligomers and for a new an improved method of preparing of polycarbonates.

According the invention the chemically resistant materials with high mechanical properties are provided by using polycyclocarbonates of special structure. The polycyclocarbonates are prepared by the reaction of oligocyclocarbonates containing ended epoxy groups with primary aromatic diamine.

One embodiment of the present invention relates to oligomers containing epoxy and cyclocarbonate groups, adduct of aromatic diamines with these oligomers. Such oligomers may be used by two ways—by curing the oligomers with primary aliphatic amines and by preparing adducts which are used for curing epoxy resins or cyclocarbonate oligomers for preparing constructive glues, sealants, coatings, construction, etc.

The new polyfunctional polycyclocarbonate oligomers of the present invention can be defined by the formula:

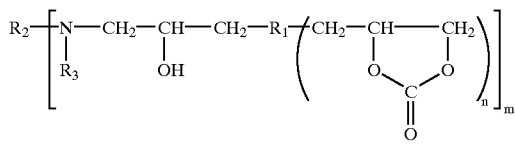

wherein: $R_1$—aliphatic, cycloaliphatic, aromatic, alkylaromatic, oligoester or oligoether radicals $R_2$—aromatic radicals $R_3$—H, alkyl, aryl, alkylaryl m=1–2; n=1–5

The method of preparing of new polyfunctional polycyclocarbonates comprises reacting a compound of the formula:

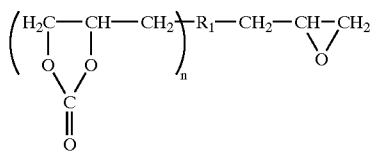

with primary aromatic diamines by stoichiometric ratio to epoxy groups.

The method also includes carrying out the reaction at a temperature from 100° C. to 150° C. both in "situ" and in an organic solvent.

The method also includes using oligomers, chosen from the group which includes oligomer's having the following structures:

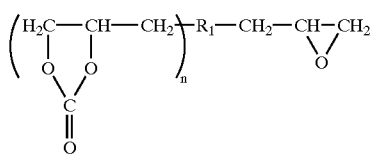

where $R_1$=

1. —O—[(CH$_2$)$_k$—O]$_y$—
   k=2–6, y=1–20, n=1
2.

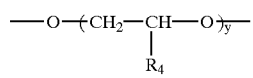

where: $R_4$=$CH_3$, $C_2H_5$ y=1–20, n=1

3.
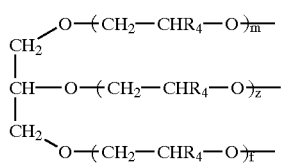
where: $R_4$=H, $CH_3$
$m+z+f=0–50$
$n=2$
4.
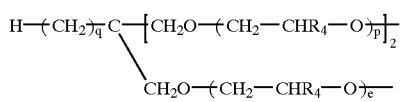
where: $R_4$=H, $CH_3$
$p+e=0–50$
$q=1–2$
$n=2$
5.
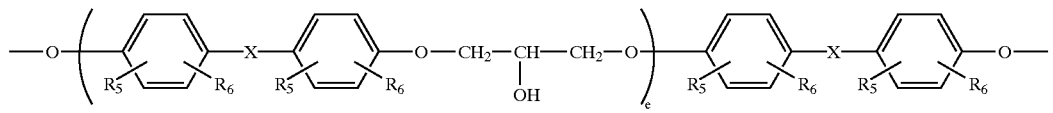
where: $X$=—$C_2$—, $(CH_3)_2C$=, —$SO_2$—, $(CF_3)_2C$=;
$R_5$, $R_6$=—H, —$CH_3$, —Cl, —Br; $e=0–5$, $n=1$
6.
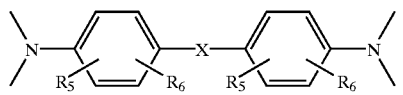
where: $X$=—$CH_2$—, $(CH_3)_2C$=, —$SO_2$—,
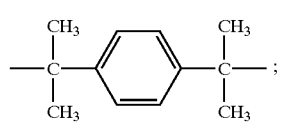
$R_5$, $R_6$=—H, —$CH_3$, —Cl; $n=3$
7.
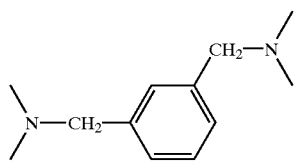
$n=3$
8.
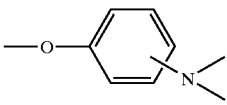
$n=2$
9.
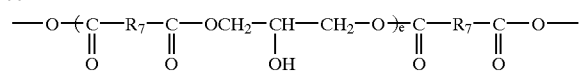
where:
$R_7$ = 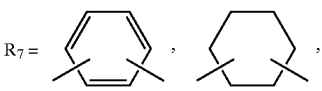,
—$(CH_2)_m$—; $e=0–2$, $n=1$
10.
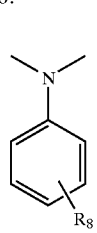
where: $R_8$=—H, —$CH_3$, —Br, —Cl;
$n=1$
11.
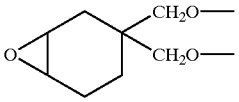
$n=1$
12.
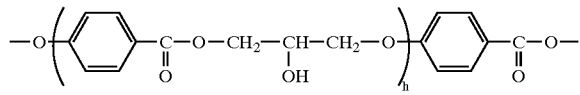
$h = 0–2$  $n = 1$ 13.
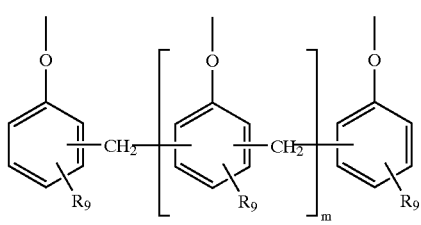
where: $R_9$=—H, —$CH_3$; m=1–5, n=2–6
14.
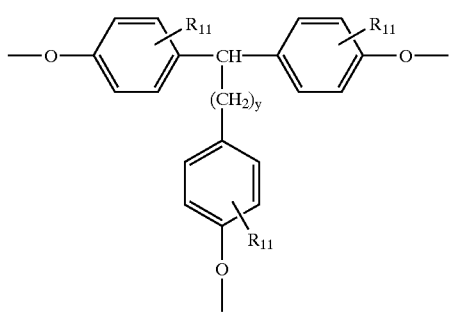
where: $R_{11}$=—H, —$CH_3$;
y=1–2, n=2
15.
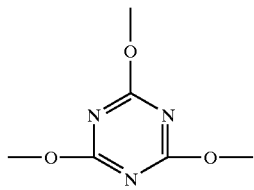
n=1
16.
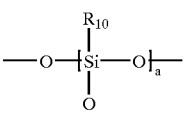
where: $R_{10}$= —$CH_3$, —;
a = 1–4, n = 2–5
17.
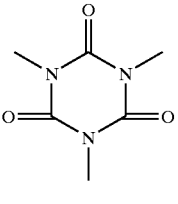
n = 2
18.
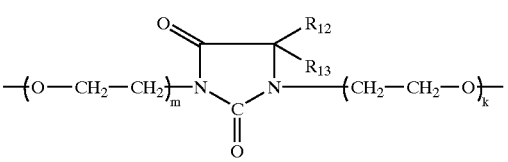
where: $R_{12}$, $R_{13}$=H, $CH_3$; m+k=0–6, n=1
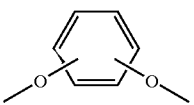
n=1
The method also includes preferably using oligomers, chosen from the following group:
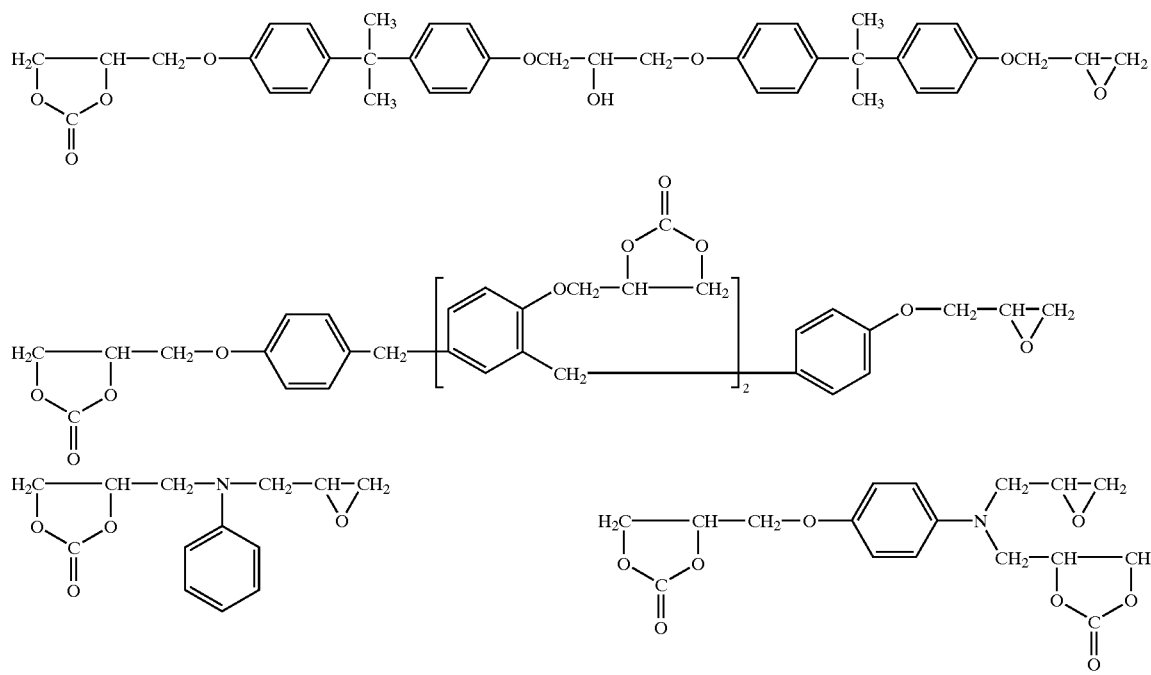

-continued

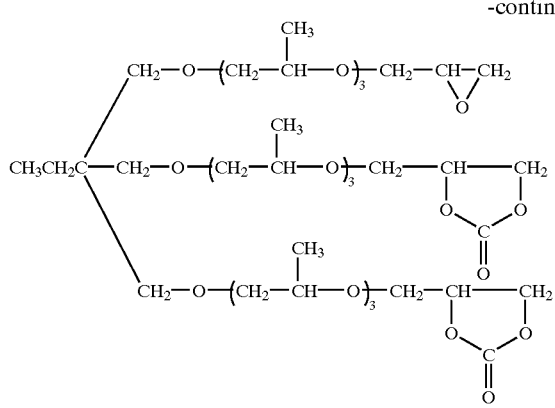

The method also includes using aromatic diamines, chosen from the groups, which contain:

$$H_2N-R-NH_2$$

where R:=

where: $R_1$=—$CH_3$, —Cl;

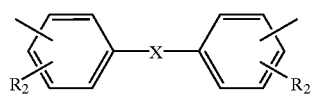

where: X=—$CH_2$, $(CH_3)_2$=,

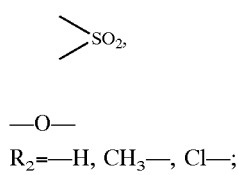

—O—

$R_2$=—H, $CH_3$—, Cl—;

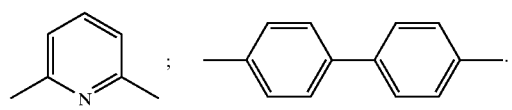

The method also includes preferably using aromatic diamines, chosen from the group, which contain:

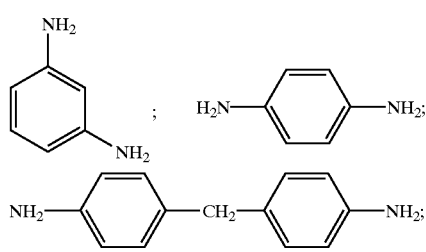

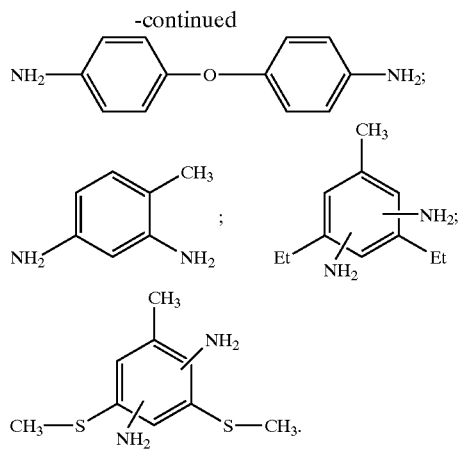

The present invention also includes using of polyfunctional Cyclocarbonate Oligomers for preparing amine hardeners having ended aminoalkyl groups:

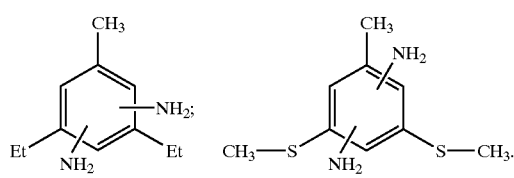

DETAILED DESCRIPTION OF THE INVENTION

Polycyclocarbonate oligomers of the present invention are based upon oligomers with epoxy and cyclocarbonate groups which ware prepared by the reaction of carbon dioxide and an epoxy oligomer with catalyst according our pat. (Patent Israel 122763)

Such oligomers containing epoxy and cyclocarbonate groups react with aromatic diamines only by epoxy groups. It is possible to cure such cyclocarbonate oligomers by primary aliphatic amines and to prepare adducts of synthesised cyclocarbonates with primary aliphatic amines that are used as hardeners for epoxy oligomers.

For preparing polycyclocarbonate oligomers are used epoxy-cyclocarbonate olygomers preferably of such formula:

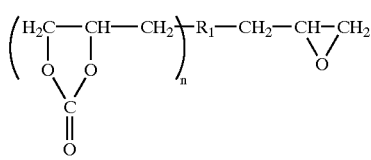

Suitable commercially available epoxy resins
DER-324, DER-332, DEN-431, DER-732 Dow Chemical Co (USA),
EPON 813, EPON 8021, EPON 8091,
EPON 825, EPON 828 Shell Chemical Co (USA),
NPEF-165 Nan Ya Plastic Corporation (R. China),
PEP 6180, PEP 6769, PEP 6760 Pacific Epoxy Polymers, Inc (USA),
Araldite 0510, MY-0501, MY-720 Ciba-Geigy A.G. (USA),
Laprolat 803, 703 "Macromer" Ltd. (Russia),
Ricopoxy 30 Ricon Resins Inc. (USA)

Preferably commercially available aromatic diamines: m-phenylendiamine, 4,4'-diaminodiphenylmethane, 4,4'-diaminodiphenyloxide, 2,4 and 2,6 diethyltoluelenediamine (Albermnarle Corporation).

Preferably commercially available primary amines: N,N-bis(3-aminopropyl) methylamine (BASF, Germany), m-xylylenediamine (Mitsubishi, Japan), triethyleneglycoldiamine (Jeffamine), EDR-148 (Huntsman Corporation, USA), 1,3-diaminopentane (Du Pont, USA), Isoforondiamine (BASF, Germany), Jeffamine T-403 (Huntsman Corporation, USA), etc.

EXAMPLES

The following examples of oligocyclocarbonates and also materials based on them are given to illustrate the present invention. However, it is to be understood that the examples are for illustrative purposes only and in no manner is the present invention limited to the specific disclosure therein.

Example 1

Preparing Polycyclocarbonate Oligomers

Ten sample compositions of the invention were prepared by the following method. The components formulated into each sample and the amounts used are shown in Table 1.

Synthesis is a reaction between epoxy group of the oligomer and aromatic diamines. Such process is working out in special glass reactor under $N_2$. Contents are mixed during 10 min at the 20° C., after that the reaction continues during 0,5–1 hr by the 120–130 ° C. After this operation according with Table 1 primary amines are mixed with compounds after that the reaction continues during 2 hrs by the 110–120° C. (samples 1,3,5,7,9). After that the oligomers are mixed with epoxy resins for curing (according Table 1).

Oligomers (samples 2,4,6,8,10) are mixed with primary amines according Table 1 for curing.

For preparing coatings were used 80% solution in dimethylformnamide.

Additionally, certain control samples were also prepared by the above method.

Composition 1c is identical to Composition 1 except that epoxy-cyclocarbonate oligomer with EEW=331; CC EW=615.4 was used in the reaction of oligomerisation.

Composition 2c is identical to Composition 1 except that epoxy-cyclocarbonate olygomer with EEW=653; CC EW=352 was used in the reaction of oligomerisation.

Composition 3c is identical to Composition 3 except that epoxy-cyclocarbonate olygomer with EEW=248; CC EW=744 was used in the reaction of oligomerisation.

Composition 4c is identical to Composition 4 except that epoxy-cyclocarbonate oligomer with EEW=2000; CC EW=240 was used in the reaction of oligomerisation.

Composition 5c is identical to Composition 5 except that epoxy-cyclocarbonate oligomer with EEW=921; CC EW=196 was used in the reaction of oligomerisation.

TABLE 1

Compositions (in parts by weight based on 100 parts epoxy-cyclocarbonate oligomer)

| Composition | 1 | 2 | 3 | 4 | 5 | 6 | 7 | 8 | 9 | 10 |
|---|---|---|---|---|---|---|---|---|---|---|
| Epoxy-Cyclocarbonate oligomer based on BHPA epoxy resin D.E.R.-324 (Dow Chemical Co) EEW = 444 CC EW = 444 | 100 | 100 | — | — | — | — | — | — | — | — |
| Epoxy-Cyclocarbonate oligomer based on Novolac Resin D.E.N.-431 (Dow Chemical Co) EEW = 569 CC EW = 316 | — | — | 100 | 100 | — | — | — | — | — | — |
| Epoxy-Cyclocarbonate oligomer based on Methylen-bis(o-ethylaniline) XUMY-722 (Ciba-Geigy) EEW = 632 CC EW = 211 | — | — | — | — | 100 | 100 | — | — | — | — |
| Epoxy-Cyclocarbonate oligomer based on aniline PEP 6760 (Pacific Epoxy Polymers) EEW = 264 CC EW = 264 | — | — | — | — | — | — | 100 | 100 | — | — |
| Epoxy-Cyclocarbonate oligomer Based on trimethylol propane, oxide propylene, epychlorhydrine Laprolate (Macromer Ltd. Russia) EEW = 1038 CCEW = 519 | — | — | — | — | — | — | — | — | 100 | 100 |
| m-Phenylenediamine Mw 108.1 | 12.2 | | 9.5 | | | | | | | |

TABLE 1-continued

Compositions (in parts by weight based on 100 parts epoxy-cyclocarbonate oligomer)

| Composition | 1 | 2 | 3 | 4 | 5 | 6 | 7 | 8 | 9 | 10 |
|---|---|---|---|---|---|---|---|---|---|---|
| 4,4'-diaminodiphenylmethane Mw 198.3 | | 22.3 | | 17.4 | | | | | | |
| 4,4'-diaminodiphenyloxide Mw 200 | | | | | 15.8 | | 37.9 | | | |
| 3,4-toluenediamine Mw 122.2 | | | | | | 9.7 | | 23.1 | | 5.9 |
| 2,4 & 2,6 diethyltoluelenediamine Ethacure 100 Albermarle Corporation Mw 178 | | | | | | | | | 8.6 | |
| Molecular weight of adduct | 996 | 1086.3 | 1246.1 | 1322.3 | 1486 | 1386.2 | 728 | 650.2 | 2254 | 2198.2 |
| N, Nbis(3-aminopropyl)methylamine Mw 146 (BASF) | 32.9 | 16.4 | 46.2 | 23.3 | — | — | — | — | — | — |
| M-xylelenediamine Mw 132 (Mitzubishi) | — | — | — | — | 61.7 | 31.3 | 50 | 25.0 | 25.4 | 6.4 |
| Epoxy oligomer DER-324 (Dow Chemical) EEW 200 | 90 | — | — | — | 18.7 | — | — | — | — | — |
| Epoxy novolac olygomer DEN 431 (Dow Chemical) EEW 175 | — | — | 110.7 | — | — | — | 132.6 | — | 67.4 | — |

Composition 6c is identical to composition 6 except that epoxy-cyclocarbonate oligomer with EEW=161; CC EW=758 was used in the reaction of oligomerisation.

Composition 7c is identical to composite 7 except that epoxy-cyclocarbonate oligomer with EEW=193; CC EW=358 was used in the reaction of oligomerisation.

Composition 8c is identical to composite 8 except that epoxy-cyclocarbonate oligomer with EEW=396; CC EW=213 was used in the reaction of oligomeuisation.

Composition 9c is identical to composite 9 except that epoxy-cyclocarbonate oligomer with EEW=426; CC EW=1401 was used in the reaction of oligomerisation.

Composition 10c is identical to composite 10 except that epoxy-cyclocarbonate oligomer with EEW=1502; CC EW=457 was used in the reaction of oligomerisation.

Example 2

Preparing NIPU Coatings

Cyclocarbonate oligomers (1–10) prepared according the method described in Example 1 were used to coat a cleaned steel plate. Each composition formed a coating layer with a thickness of 0,1–0,2 mm. Then the coating was hardened at a temperature 110° C. for 2 hours. These coated steel samples were used to determine the adhesion of each coating to the steel substrate according to the method prescribed by ASTM D3359-93. Compositions were used as 80% solution in dimethylformamide. For the purposes of tensile testing, the above procedure was modified by using a polytetrafluoroethylene (PTFE) sheet instead of steel plate, so a free film of each of the 10 cyclocarbonate-oligomers could be obtained by peeling the PTFE from the cured film. The tensile properties, i.e. tensile strength and elongation at break, of each free cured film were determined according to the method prescribed by ASTM D638-84. Such samples were also used to determine the coefficient of chemical resistance of each coating by the procedure discussed above in which the tensile strength was used to determine $K_{CR}$.

The properties of ten coatings of the invention, samples 11–20, are shown in Table 2.

The properties of ten coatings, samples 21–30, are also formed by the above described method are shown in Table 3.

TABLE 2

Properties of Cured Oligomer Coatings

| Sample N° | 11 | 12 | 13 | 14 | 15 | 16 | 17 | 18 | 19 | 20 |
|---|---|---|---|---|---|---|---|---|---|---|
| Composition N° | 1 | 2 | 3 | 4 | 5 | 6 | 7 | 8 | 9 | 10 |
| Tensile strength, MPa | 98 | 87 | 96 | 97 | 110 | 100 | 95 | 93 | 111 | 103 |
| Elongation at Break, % | 2 | 2,5 | 2.2 | 2 | 2 | 2.2 | 2.3 | 2.2 | 4 | 3.5 |
| Adhesion, ASTM D 3359 | 4B | 4B | 4B | 4B | 4B | 4B | 4B | 4B | 4B | 4B |
| KCR after 180 days at 60° C in: | | | | | | | | | | |
| 10% Aqueous Hydrochloric Acid | 0.86 | 0.9 | 0.88 | 0.98 | 0.9 | 0.93 | 0.9 | 0.9 | 0.9 | 0.9 |
| 10% Aqueous NaOH | 0.80 | 0.85 | 0.87 | 0.83 | 0.9 | 0.87 | 0.88 | 0.85 | 0.83 | 0.82 |
| 10% Aqueous NaCl | 0.90 | 0.91 | 0.87 | 0.92 | 0.91 | 0.93 | 0.94 | 0.89 | 0.85 | 0.87 |

TABLE 3

Properties of Cured Control Coatings

| Sample N° | 21 | 22 | 23 | 24 | 25 | 26 | 27 | 28 | 29 | 30 |
|---|---|---|---|---|---|---|---|---|---|---|
| Composition N° | 1c | 2c | 3c | 4c | 5c | 6c | 7c | 8c | 9c | 10c |
| Tensile Strength, MPa | 75 | 65 | 71 | 80 | 81 | 95 | 85 | 87 | 96 | 60 |
| Elongation at Break, % | 1 | 5 | 1 | 4 | 4 | 1 | 3 | 3 | 3 | 5 |
| Adhesion | 3B | 3B | 3B | 3B | 3B | 3B | 3B | 3B | 3B | 3B |

The proposed oligomers may be used for preparing adhesives, sealants, synthetic foams, synthetic leathers, hardeners for epoxy resins, casting elastomers, structure plastics, etc.

The possible areas of applications are illustrated by following examples. Adhesives based on the compositions 1–10 (table 1) can be used as structure adhesives with high service properties. The adhesives compositions have been received by adding to adducts (1, 3, 7 or 9) epoxy resins, which are using here as a hardener. By using the compositions 2, 3, 4 and 6–10 addition adding epoxy resins does not needed. Such method of Adhesives preparing gives adhesives joints with more shock and vibration resistance properties. The mechanical properties of adhesives joints were described in the table 2.

By preparing of adhesives compositions pigments and fillers can be also added. Preferable ones are barium sulfate, titanium dioxide, silica and ferrous oxides pigments and aluminate cement. By adding as a filler glass microspheres can be received synthetic foams.

Sealants can be received on the base of adducts by example 1, 3, 7. In this case are needed using another hardeners (see table 4). The properties of such sealants are given in the table 5.

On the base on oligomers according to example 1–10 can be also prepared reinforced plastics with glass, carbon or kevlar fibers and polymerconcretes with high impact, shock and abrasive resistance, with 2–3 times higher mechanical properties than those of well known unsaturated polyester reinforced plastics and concretes.

TABLE 4

Compositions for Sealants (parts by weight).

| Sample N° | 21 | 22 | 23 | 24 | 25 | 26 |
|---|---|---|---|---|---|---|
| Composition | 11 | 12 | 13 | 14 | 15 | 16 |
| Epoxy Cyclocarbonate oligomer based on BHPA epoxy resins DER-324 EEW = 444 CCEW = 444 | 100 | | | 100 | | |
| Epoxy Cyclocarbonate oligomer based on Novolac Resin DEN 431 EEW = 569 CCEW = 316 | | 100 | | | 100 | |
| Epoxy Cyclocarbonate oligomer based on aniline PER 6760 EEW = 264 CCEW = 264 | | | 100 | | | 100 |
| m-Phenilendiamine Mw 108.1 | 12.2 | 9.5 | | 12.2 | 9.5 | |

TABLE 4-continued

Compositions for Sealants (parts by weight).

| Sample N° | 21 | 22 | 23 | 24 | 25 | 26 |
|---|---|---|---|---|---|---|
| Composition | 11 | 12 | 13 | 14 | 15 | 16 |
| 4,4'-diamino diphenyl oxide Mw 200 | | | 37.9 | | | 37.9 |
| Molecular weight of adduct | 996 | 1246.1 | 728 | 996 | 1246.1 | 728 |
| N,N bis(3 amino-propyl) methylamine Mw 146 | 32.9 | 46.2 | — | 32.9 | 46.2 | — |
| m-Xylelene-diamine | — | — | 50 | — | — | 50 |
| Epoxy oligomer D.E.R.-732 EEW = 320 | 144 (50%) | 202 (56%) | 242 (56%) | | | |
| Epoxy oligomer Ricopoxy 30 EEW 717 | | | | 322 69% | 454 74% | 543 94% |

TABLE 5

Sealants Properties.

| Sample N° | 21 | 22 | 23 | 24 | 25 | 26 |
|---|---|---|---|---|---|---|
| Composition | 11 | 12 | 13 | 14 | 15 | 16 |
| Tensile strength, MPa | 6 | 55 | 55 | 45 | 40 | 42 |
| Elongation at Break, % | 80 | 100 | 95 | 400 | 500 | 600 |

11.
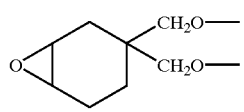
n=1
12.
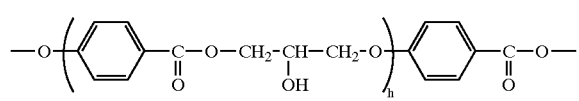
h = 0 - 2   n = 1
13.
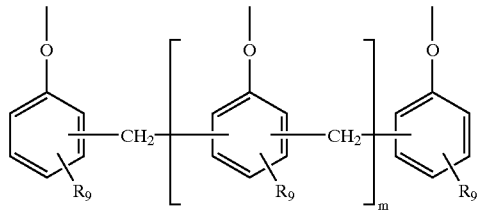
where: $R_9$ = —H, —$CH_3$; m=1–5, n=2–6
14.
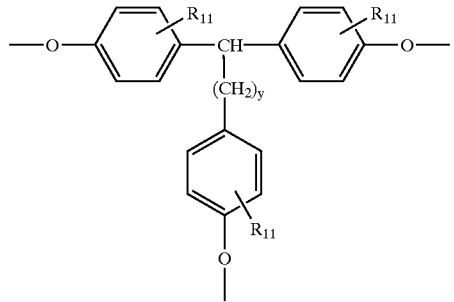
where: $R_{11}$ = —H, —$CH_3$;
y = 1 - 2, n = 2
15.
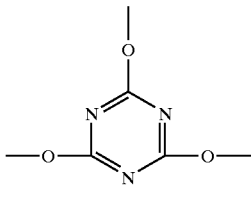
n = 1
16.
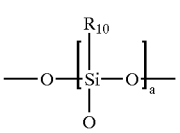
where: $R_{10}$ = —$CH_3$, 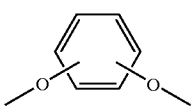,
a = 1 - 4, n = 2 - 5
17.
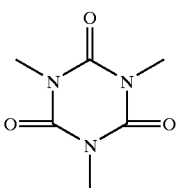
n = 2
18.
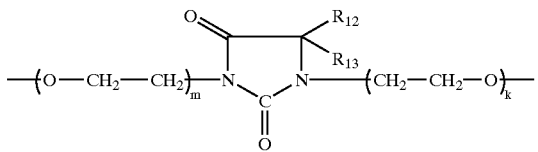
where: $R_{12}$, $R_{13}$ = H, $CH_3$; m + k = 0 - 6, n = 1
19.
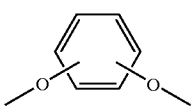
n = 1.
5. The method according to claim 2, said oligomer is chosen from the following group:
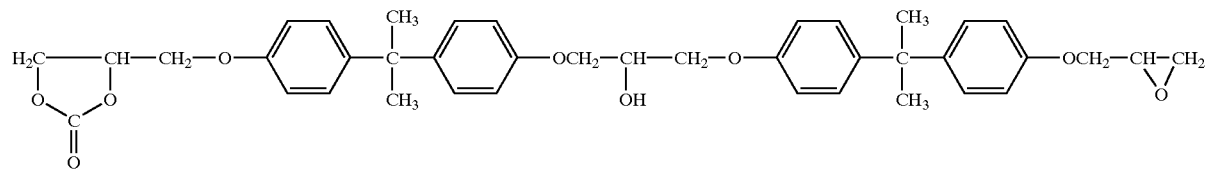

-continued
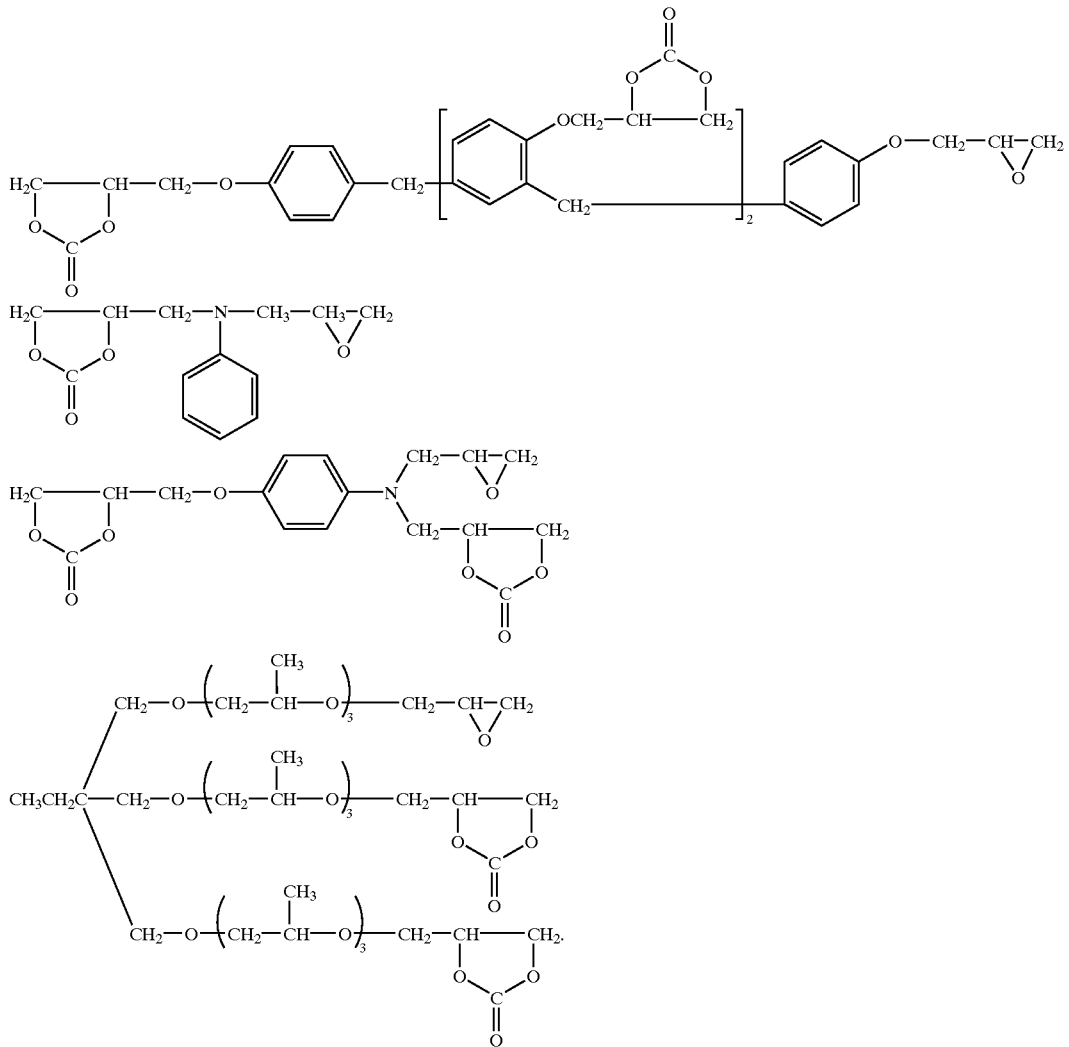
6. The method according to claim 2 wherein said aromatic diamines have a formula:
$$H_2N-R-NH_2$$
where R:=
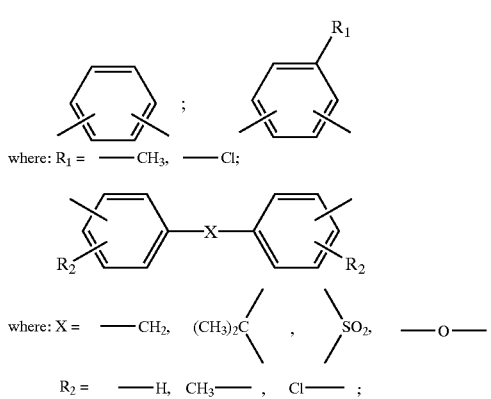
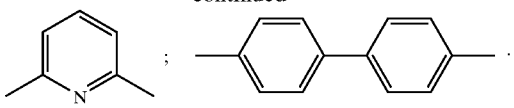
7. The method according to claim 2 wherein said aromatic diamines are chosen from the group, which contain:
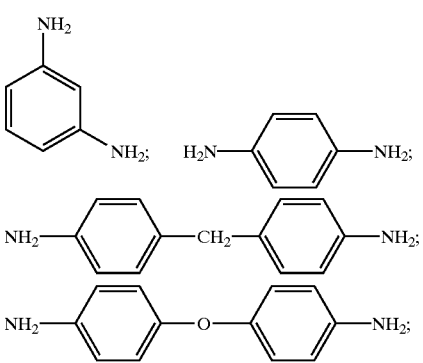

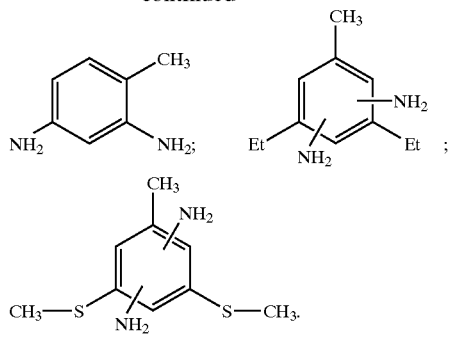
8. A method for preparing amine hardeners having ended aminoalkyl groups using a polyfunctional cyclocarbonate oligomer wherein said amine hardeners have an ended aminoalkyl group of the formula:
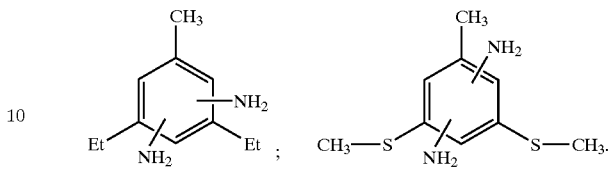

What is claimed is:

1. Polyfunctional polycyclocarbonate oligomers having a formula:

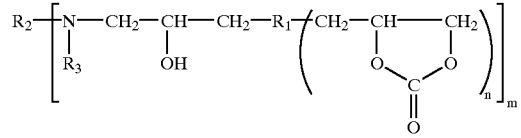

where: $R_1$—aliphatic, cycloaliphatic, aromatic, alkylaromatic, oligoester or oligoether radicals
$R_2$—aromatic radicals
$R_3$—H, alkyl, aryl, alkylaryl
m=1–2; n=1–5.

2. A method of preparing of polyfunctional polycyclocarbonates comprising reacting an oligomer of the formula:

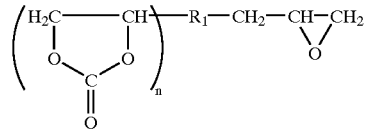

with primary aromatic diamines by stoichiometric ratio to epoxy groups.

3. The method according to claim 2 wherein the reaction is carried out at a temperature from 100° C. to 150° C. both in "situ" and in an organic solvent.

4. The method according to claim 2 wherein $R_1=$

1. $-O-[(CH_2)_k-O-]_y$ k=2–6, y=1–20, n=1

2.

$$-O-(CH_2-CH(R_4)-O)_y-$$

where: $R_4=CH_3, C_2H_5$ y=1–20, n=1

3.

$$\begin{array}{l} CH_2-O-(CH_2-CHR_4-O)_m- \\ CH-O-(CH_2-CHR_4-O)_z- \\ CH_2-O-(CH_2-CHR_4-O)_f- \end{array}$$

where: $R_4=H, CH_3$
m+z+f=0–50
n=2

4.

$$H-(CH_2)_q-C-[CH_2O-(CH_2-CHR_4-O)_p]_2$$
$$CH_2O-(CH_2-CHR_4-O)_e-$$

where: $R_4=H, CH_3$
p+e=0–50
q=1–2
n=2

5.

[structure: $-O-(\text{Ar}-X-\text{Ar}-O-CH_2-CH(OH)-CH_2-O-)_e-\text{Ar}-X-\text{Ar}-O-$ with $R_5, R_6$ substituents]

where: $X=-CH_2-, (CH_3)_2C=, -SO_2-,$ $(CF_3)_2C\diagup\diagdown$ ;

$R_5, R_6=-H, -CH_3, -Cl, -Br$; e=0–5, n=1

6.

[structure: $(CH_3)_2N-\text{Ar}-X-\text{Ar}-N(CH_3)_2$ with $R_5, R_6$ substituents]

where: $X=-CH_2-,$ $(CH_3)_2C\diagup\diagdown$ , $-SO_2-,$

[structure: $-C(CH_3)_2-\text{Ar}-C(CH_3)_2-$]

$R_5, R_6=-H, -CH_3, -Cl$; n=3

[structure: 1,3-bis(dimethylaminomethyl)benzene]

n = 3

[structure: $-O-\text{Ar}-N(CH_3)_2$]

n = 2

$$-O-C(=O)-R_7-C(=O)-OCH_2-CH(OH)-CH_2-O)_e-C(=O)-R_7-C(=O)-O-$$

where:

$R_7 = $ [phenylene], [cyclohexylene], $-(CH_2)_m-$; e=0–2, n=1

10.

[structure: $(CH_3)_2N-\text{Ar}-R_8$]

where: $R_8=-H, -CH_3, -Br, -Cl$;
n=1